(12) United States Patent
Bharat et al.

(10) Patent No.: US 11,266,374 B2
(45) Date of Patent: Mar. 8, 2022

(54) DEVICE FOR INTERVENTIONAL ACOUSTIC IMAGING

(71) Applicant: KONINKLIJKE PHILIPS N.V., Eindhoven (NL)

(72) Inventors: Shyam Bharat, Cambridge, MA (US); Ramon Quido Erkamp, Cambridge, MA (US); Man Nguyen, Cambridge, MA (US); Jean-Luc Robert, Cambridge, MA (US); Sheng-Wen Huang, Cambridge, MA (US); Jochen Kruecker, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 348 days.

(21) Appl. No.: 16/066,323

(22) PCT Filed: Dec. 30, 2016

(86) PCT No.: PCT/EP2016/082935
§ 371 (c)(1),
(2) Date: Jun. 27, 2018

(87) PCT Pub. No.: WO2017/114956
PCT Pub. Date: Jul. 6, 2017

(65) Prior Publication Data
US 2019/0021693 A1    Jan. 24, 2019

Related U.S. Application Data

(60) Provisional application No. 62/273,667, filed on Dec. 31, 2015.

(30) Foreign Application Priority Data

Feb. 29, 2016  (EP) ..................................... 16157783

(51) Int. Cl.
*A61B 8/08*        (2006.01)
*A61B 8/00*        (2006.01)
(Continued)

(52) U.S. Cl.
CPC .......... *A61B 8/0841* (2013.01); *A61B 8/4411* (2013.01); *A61B 8/4455* (2013.01);
(Continued)

(58) Field of Classification Search
CPC ... A61B 8/0841; A61B 8/4494; A61B 8/4411; A61B 8/4455; A61B 2034/2051;
(Continued)

(56) References Cited

U.S. PATENT DOCUMENTS 4,029,084 A    6/1977  Soldner
4,289,139 A *  9/1981  Enjoji .................. A61B 8/0833
                                                         600/461
(Continued)

FOREIGN PATENT DOCUMENTS

JP    2010197897 A    9/2010
JP    2011104052 A    6/2011
(Continued)

*Primary Examiner* — Christopher Koharski
*Assistant Examiner* — Kaitlyn E Selmer

(57) ABSTRACT

An acoustic probe connectable to an imaging system. The acoustic probe has a substrate with first and second principal surfaces, at least one device insertion port comprising an opening passing through the substrate from the first principal surface to the second principal surface, and an array of acoustic transducer elements supported by the substrate and disposed around the at least one device insertion port. The acoustic probe comprising an instrument guide disposed within the device insertion port, the instrument guide being configured to selectively allow the interventional device to move freely within the device insertion port and to selectively lock the interventional device within the device inser- (Continued)

tion port in response to a user input via a user interface connected to the acoustic probe.

26 Claims, 12 Drawing Sheets

(51) Int. Cl.
   *A61B 34/20* (2016.01)
   *A61B 17/34* (2006.01)
(52) U.S. Cl.
   CPC .... *A61B 8/4494* (2013.01); *A61B 2017/3407* (2013.01); *A61B 2017/3413* (2013.01); *A61B 2034/2051* (2016.02); *A61B 2034/2059* (2016.02)
(58) Field of Classification Search
   CPC .... A61B 2034/2055; A61B 2034/2059; A61B 2017/3407; A61B 2017/3413
   See application file for complete search history.

(56) References Cited

U.S. PATENT DOCUMENTS

| | | | |
|---|---|---|---|
| 4,870,867 A | | 10/1989 | Shaulov |
| 5,289,139 A | | 2/1994 | Fiedziuszko et al. |
| 6,132,379 A | * | 10/2000 | Patacsil ................ A61B 8/06 600/459 |
| 2004/0089083 A1 | * | 5/2004 | Bailey ................ G01D 5/34 74/5.4 |
| 2005/0080328 A1 | | 4/2005 | Vass et al. |
| 2005/0101868 A1 | * | 5/2005 | Ridley ................ A61B 8/4444 600/459 |
| 2005/0187538 A1 | | 8/2005 | Boese et al. |
| 2007/0167742 A1 | * | 7/2007 | Wurmfeld .......... G01D 5/34723 600/424 |
| 2012/0022508 A1 | | 6/2012 | Gross et al. |
| 2012/0323247 A1 | * | 12/2012 | Bettenga ................ A61F 2/46 606/91 |
| 2013/0267963 A1 | * | 10/2013 | Golden ................ A61B 90/11 606/130 |
| 2014/0148701 A1 | | 5/2014 | Yao et al. |
| 2014/0243668 A1 | | 8/2014 | Varghese et al. |
| 2014/0276082 A1 | * | 9/2014 | Janicki ................ A61B 17/3403 600/461 |
| 2015/0320439 A1 | * | 11/2015 | Andrews ................ A61B 8/523 600/461 |
| 2016/0007979 A1 | * | 1/2016 | Bhagat ................ A61B 17/3494 604/175 |
| 2016/0337634 A1 | * | 11/2016 | Huemoeller .......... G03B 15/00 |

FOREIGN PATENT DOCUMENTS

| | | |
|---|---|---|
| JP | 2014174877 A | 9/2014 |
| WO | 2006035160 A1 | 4/2006 |
| WO | 2009069038 A1 | 6/2009 |
| WO | 2017114701 A1 | 7/2017 |
| WO | 2017114956 A1 | 7/2017 |

* cited by examiner

DEVICE FOR INTERVENTIONAL ACOUSTIC IMAGING

This application is the U.S. National Phase application under 35 U.S.C. § 371 of International Application No. PCT/EP2016/082935 filed on Dec. 30, 2016, which claims the benefit of Provisional Application Ser. No. 62/273,667 filed Dec. 31, 2015 and EP Application Serial No. 16157783.8, filed Feb. 29, 2016. These applications are hereby incorporated by reference herein.

TECHNICAL FIELD

This invention pertains to acoustic (e.g., ultrasound) imaging, and in particular a device and method for acoustic imaging in conjunction with an interventional procedure.

BACKGROUND AND SUMMARY

Acoustic (e.g., ultrasound) imaging systems are increasingly being employed in a variety of applications and contexts. For example, ultrasound imaging is being increasingly employed in the context of minimally invasive surgeries. This includes needle based procedures such as Chorionic Villus Sampling (CVS), needle based biopsies, and nerve blocks for local anesthesia. Today, typically the imaging probes that are used in minimally invasive interventional procedures have an imaging array configuration that is identical to that of the probes used in diagnostic imaging.

Visualization of an interventional device, or devices, (e.g., surgical instrument(s)) employed in these procedures using existing acoustic probes and imaging systems is challenging in many cases, and often requires manual repositioning of the acoustic probe during the procedure to maintain sufficient image quality. A significant percentage of CVS procedures are described by the physician as difficult, and an even greater percentage are reported to have involved more than one insertion.

To address these problems, special interventional devices, such as echogenic needles, with enhanced visibility are successfully on the market and provide limited improvement at moderate extra cost. More progress in needle visualization has recently been made in the form of needle tracking technologies, based on magnetic tracking or stereoscopic cameras with optical fiducials. These visualization techniques could also be applied to other interventional devices Even with these improvements, certain clinical applications (e.g., deep nerve block) still remain largely or completely out of reach because of certain limitations to existing acoustic imaging probes and systems. In many cases, anatomical features at the intervention site cannot be sufficiently resolved, especially for procedures which are performed at greater depths beneath the skin surface. For example, acoustic imaging guidance is used in shallow nerve blocks (e.g., up to depths of 3 cm) and is able to visualize the nerves in such procedures. Acoustic imaging is also employed for deep nerve, but because existing systems cannot visualize these nerves, physicians use anatomical landmarks as guidance, making deep blocks much harder to perform. Instrument visualization also can be poor due to specular reflection of device surface. Furthermore, during ultrasound guided interventional procedures, one does not want to have to manipulate the position of the imaging probe.

Clearly there are already many existing applications for interventional ultrasound, and additional applications could be realized with improvements in device and anatomy visualization and in operating characteristics. Such applications may include cancer ablation procedures, CVS, fetal surgeries/interventions (e.g., altering blood flow patterns in twin-to-twin transfusion syndrome (TTTS)), liver biopsies, and deep nerve block procedures.

Desirable attributes for an acoustic imaging system and method include: accurate visualization of the instrument in the ultrasound image; enhanced imaging resolution at the location of intervention; and hands free operation of the acoustic probe.

Document US 2005/0101868 discloses an ultrasound device that includes an ultrasound transducer housing having a passage therethrough configured to accommodate a probe.

Accordingly, it would be desirable to provide an ultrasound system, an acoustic probe, and a method which can provide enhanced acoustic imaging capabilities during interventional procedures.

In one aspect of the invention, a system comprises: an acoustic probe having: a substrate having first and second principal surfaces, and further having at least one device insertion port comprising a tapered opening passing through the substrate from the first principal surface to the second principal surface, and an array of acoustic transducer elements supported by the substrate and disposed around the at least one device insertion port; and an acoustic imaging machine connected to the acoustic probe and configured to provide transmit signals to least some of the acoustic transducer elements to cause the array of acoustic transducer elements to transmit an acoustic probe signal to an area of interest, and further configured to produce acoustic images of the area of interest in response to one or more signals received from the acoustic probe in response to acoustic echoes received by the acoustic probe from the area of interest.

In some embodiments, the acoustic imaging machine is further configured to receive a feedback signal from an acoustic receiver provided at a distal end of an interventional device passes through the device insertion port into the area of interest.

In some versions of these embodiments, the acoustic imaging machine is further configured to use the feedback signal from the acoustic receiver to register a location of the acoustic receiver with respect to the acoustic echoes received by the acoustic probe, and to use the registration to mitigate aberration artifacts in the acoustic images In some embodiments, the substrate has a shape of a concave disc, and wherein an active area of the substrate defined by the array of acoustic transducer elements has a diameter of at least approximately 12 cm.

In some versions of these embodiments, the system is configured to provide an active acoustic aperture at a given time of at least approximately 10 cm, and is further configured to slide the active acoustic aperture over a range of at least approximately 2 cm in an elevation direction and in a lateral direction over time In some versions of these embodiments, the center frequency of the acoustic probe signal is about 3.5 MHz, and wherein at least some of the acoustic transducer elements have a size which is approximately 0.44 cm.

In another aspect of the invention, a method comprises: providing an acoustic probe comprising a substrate configured to be applied to the skin of a subject, the substrate having first and second principal surfaces with a diameter of at least approximately 12 cm and a shape of a concave disc which conforms to a shape of the skin where the acoustic probe is applied, the acoustic probe further having at least one device insertion port comprising an opening passing through the substrate from the first principal surface to the second principal surface, and an array of acoustic transducer elements supported by the substrate and disposed around the at least one device insertion port; providing transmit signals to least some of the acoustic transducer elements; the array of acoustic transducer elements transmitting an acoustic probe signal to an area of interest in the subject in response to the transmit signals; receiving at the acoustic probe acoustic echoes from the area of interest; receiving a feedback signal from an acoustic receiver provided at a distal end of an interventional device which passes through the device insertion port; using the feedback signal from the acoustic receiver to register a location of the acoustic receiver with respect to the acoustic echoes received by the acoustic probe; producing acoustic images of the area of interest in response to one or more signals received from the acoustic probe in response to the received acoustic echoes; and using the registration of the location of the acoustic receiver with respect to the acoustic echoes to mitigate aberration artifacts in the acoustic images.

In some embodiments, the center frequency of the acoustic probe signal is about 3.5 MHz, and wherein the area of interest includes an area about 8 cm beneath the skin.

In some versions of these embodiments, the method further comprises the acoustic probe selectively allowing the interventional device to move freely within the device insertion port, and locking the interventional device within the device insertion port, in response to a user input via a user interface associated with the acoustic probe.

In some versions of these embodiments, the method further comprises receiving from a user via a user interface an indication of a target location in the area of interest for the interventional device to be located; computing an orientation of an instrument guide disposed in the device insertion port which will enable the interventional device passing through the device insertion port to reach the target location; and maneuvering the instrument guide to the computed orientation.

In some versions of these embodiments, a controller controls the instrument guide to automatically maneuver the instrument guide to the computed orientation of the instrument guide.

In some versions of these embodiments, the method further comprises when a user maneuvers the instrument guide to the computed orientation, providing feedback to the user regarding an alignment between computed orientation of the instrument guide and a current orientation of the instrument guide via one or more lighting elements disposed on the acoustic probe In some versions of these embodiments, the method further comprises maneuvering the instrument guide to the computed orientation in response to user input via a joystick attached to the instrument guide.

In yet another aspect of the invention, an acoustic probe comprises: a substrate having a shape of a concave disc and having first and second principal surfaces, and further having at least one device insertion port comprising a tapered opening passing through the substrate from the first principal surface to the second principal surface; and an array of acoustic transducer elements supported by the substrate and disposed around the at least one device insertion port.

In some embodiments, an active area of the substrate defined by the array of acoustic transducer elements has a diameter of at least approximately 12 cm.

In some embodiments, the device insertion port has a size such that an interventional device having a diameter of 1 cm can pass therethrough.

In some embodiments, the acoustic probe further comprises an instrument guide disposed within the device insertion port, the instrument guide being configured to selectively allow an interventional device to move freely within the device insertion port, and to selectively lock the interventional device within the device insertion port in response to a user input via a user interface connected to the acoustic probe.

In some versions of these embodiments, the instrument guide includes an encoder which indicates an orientation of the instrument guide within the device insertion port.

In some versions of these embodiments, the instrument guide comprises: a ball structure having a hole for an instrument to pass therethrough; and an adjustable clamp at least partially surrounding the ball structure, the adjustable clamp being mounted to an interior surface of the device insertion port, the clamp having a spherical interior surface, wherein when the adjustable clamp is loosened the ball can rotate freely within the adjustable clamp and an insertion depth of the interventional device within the instrument guide may be adjusted, and wherein when the adjustable clamp is tightened the ball structure is immobilized within the adjustable clamp and an insertion depth of the interventional device within the instrument guide is locked.

In some versions of these embodiments, the ball structure has disposed thereon an optical pattern, and wherein the adjustable clamp has an optical detector provided therein for reading the optical pattern and providing an output signal indicating an orientation of the ball structure within the adjustable clamp.

In some embodiments, the acoustic probe further comprises at least a second device insertion port comprising at least a second opening passing through the substrate from the first principal surface to the second principal surface.

In some embodiments, the device insertion port comprises an elongated slot.

DETAILED DESCRIPTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention. Herein, when something is said to be "approximately" or "about" a certain value, it means within 10% of that value.

Figure 1:
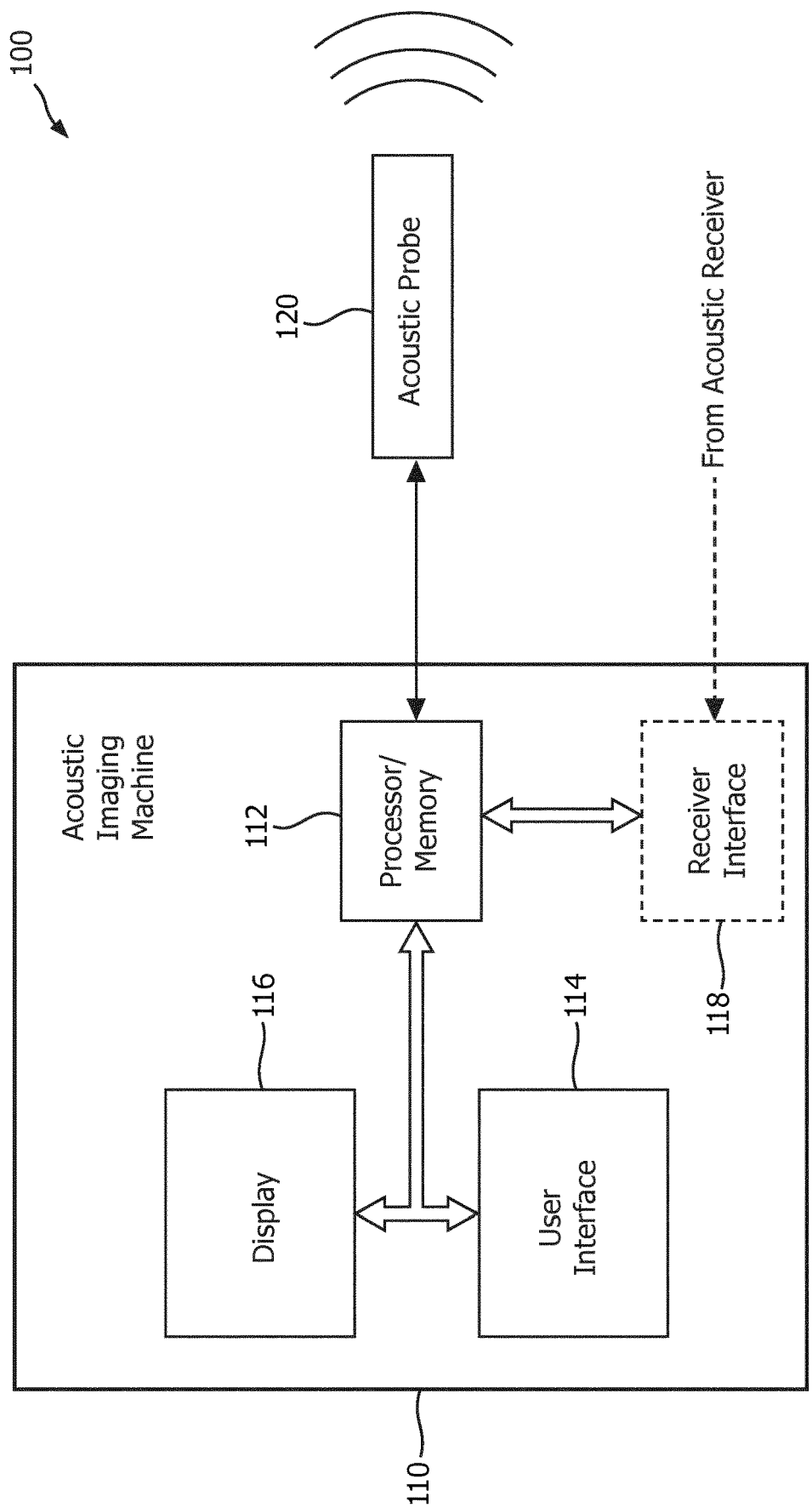
FIG. 1 shows one example of a system with an acoustic imaging machine and an acoustic probe.

FIG. 1 shows one example of an acoustic imaging system 100 which includes an acoustic imaging machine 110 and an acoustic probe 120. Acoustic imaging machine 110 include a processor (and associated memory) 112, a user interface 114, a display 116 and optionally a receiver interface 118.

In various embodiments, processor 112 may include various combinations of a microprocessor (and associated memory), a digital signal processor, an application specific integrated circuit (ASIC), a field programmable gate array (FPGA), digital circuits and/or analog circuits. Memory (e.g., nonvolatile memory) associated with processor 112 may store therein computer-readable instructions which cause a microprocessor of processor 112 to execute an algorithm to the acoustic imaging system 100 to perform one or more operations or methods which are described in greater detail below. In some embodiments, a microprocessor may execute an operating system. In some embodiments, a microprocessor may execute instructions which present a user of acoustic imaging system 100 with a graphical user interface (GUI) via user interface 114 and display 116.

In various embodiments, user interface 114 may include any combination of a keyboard, keypad, mouse, trackball, stylus/touch pen, joystick, microphone, speaker, touchscreen, one or more switches, one or more knobs, one or more lights, etc. In some embodiments, a microprocessor of processor 112 may execute a software algorithm which provides voice recognition of a user's commands via a microphone of user interface 114.

Display 116 may comprise a display screen of any convenient technology (e.g., liquid crystal display). In some embodiments the display screen may be a touchscreen device, also forming part of user interface 114.

In some embodiments, acoustic imaging machine 110 may include receiver interface 118 which is configured to receive one or more electrical signals from an external acoustic receiver, for example an acoustic receiver disposed at or near a distal end (tip) of an interventional device, as will be described in greater detail below, particularly with respect to FIG. 4.

Of course it is understood that acoustic imaging machine 110 may include a number of other elements not shown in FIG. 1, for example a power system for receiving power from AC Mains, an input/output port for communications between processor 112 and acoustic probe 120), a communication subsystem for communicating with other eternal devices and systems (e.g., via a wireless, Ethernet and/or Internet connection), etc.

Figure 2A:
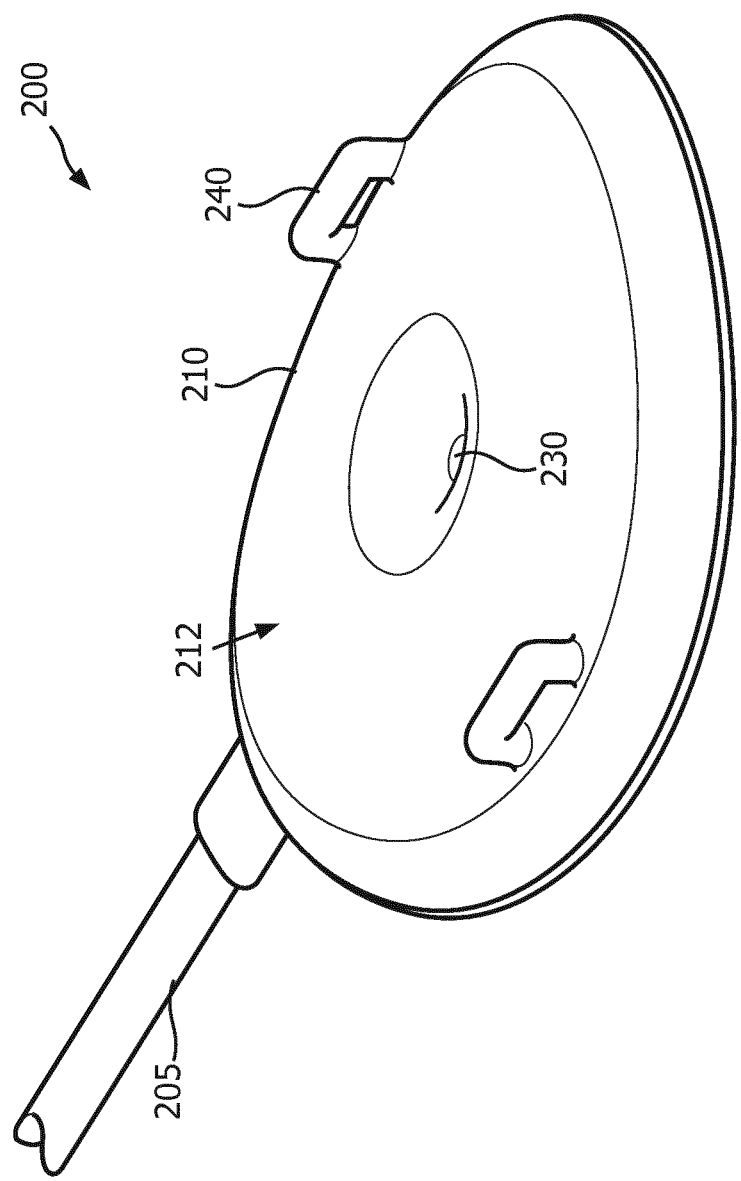
FIGS. 2A and 2B illustrate one example embodiment of an acoustic probe.
Figure 2B:
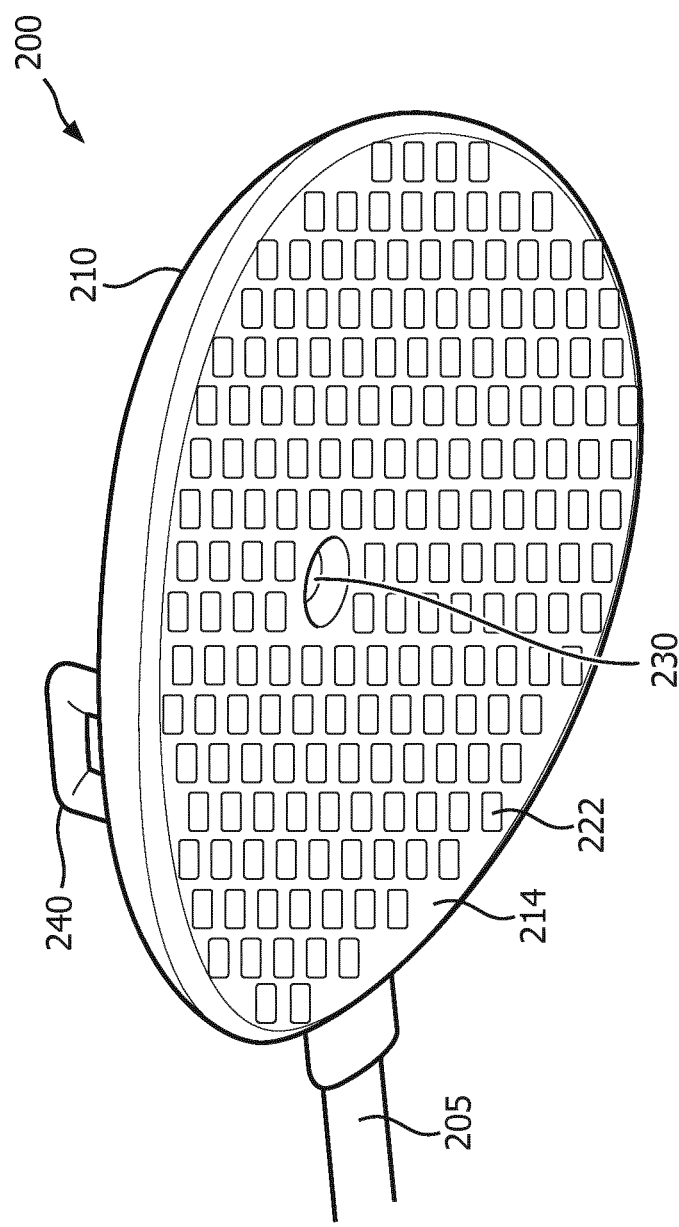

FIGS. 2A and 2B illustrate one example embodiment of an acoustic probe 200. Acoustic probe 200 may be one embodiment of acoustic probe 120 in the acoustic imaging system 100.

Acoustic probe 200 includes a substrate 210 having first and second principal surfaces 212 and 214, and further having a device insertion port 230 comprising a tapered opening passing through substrate 210 from first principal surface 212 to second principal surface 214. Acoustic probe 200 also includes an array of acoustic transducer elements 222 supported by substrate 210 and disposed around device insertion port 230. The tapered opening of the device insertion port 230 has a first diameter (d1) at the first principal surface 212 and a second diameter (d2) at the second principal surface 214, wherein the second diameter is smaller than its first diameter. The diameter of the tapered opening gradually changes from the first diameter to the second diameter while passing through the substrate 210 from the first principal surface 212 to the second principal surface 214. The tapered opening provides an interior surface of the device insertion port 230 with a conical shape, thereby enabling more flexibility for finding a suitable trajectory for inserting an interventional device into the subject's tissue without having to reposition acoustic probe. The conically shaped device insertion port 230 allows the user to vary a trajectory of insertion of the interventional device with respect to a surface of the subject's tissue. A degree of the trajectory variation (or a maximum insertion angle of the interventional device with respect to the subject's surface) would depend on a ratio between the first and the second diameters (d1/d2) of the tapered opening and/or a thickness of the substrate 210. At a given substrate thickness the maximum insertion angle increases with an increase of said ratio. In one of the aspects of the invention the second dimeter is twice as small as the first diameter. In the example shown in FIG. 2A, surface areas defined by the first and the second diameters of the tapered opening are formed concentrically at the corresponding first and second surfaces of the substrate. In some applications it may be beneficial that the device insertion port 230 comprises an opening having two surface areas at corresponding surfaces being not concentric with respect to each other. In this way the interventional tool trajectory already from the beginning of an intervention procedure may be given a predefined direction depending on the subject's anatomy.

In an aspect of the invention applicable to all disclosed embodiments disclosed therein the array of acoustic transducer elements can be disposed at a probe's side closer to (or at) the second principal surface. In this case an insertion location of the interventional tool may be more precisely defined with respect to the acoustic array due to a reduced value of the second dimeter compared to the first diameter.

Acoustic probe 200 optionally includes a pair of hooks or attachments 240 which may be used for attaching an elastic strap (e.g., via Velcro) which can go around the back of the subject to attach acoustic probe 200 to the subject.

Associated with acoustic probe 200 may be a side-mounted flat probe cable 205 which can be taped to a subject's skin during an ultrasound imaging examination of the subject, to help in further stabilizing the position of acoustic probe 200. The other end of the side-mounted flat probe cable 205 may be attached to an acoustic imaging machine (e.g., acoustic imaging machine 110 of FIG. 1) for communicating electrical signals between acoustic probe 120 and the acoustic imaging system.

Beneficially acoustic probe 200, and in particular substrate 210, including first and second principal surfaces 212 and 214, has a form factor or shape of a disc that is concavely curved to fit a subject's abdominal anatomy.

Device insertion port 230 is configured to accommodate an interventional device (e.g., surgical instrument) to pass therethrough from first principal surface 212 to second principal surface 214 and then into a subject's body at a treatment site.

Figure 3:
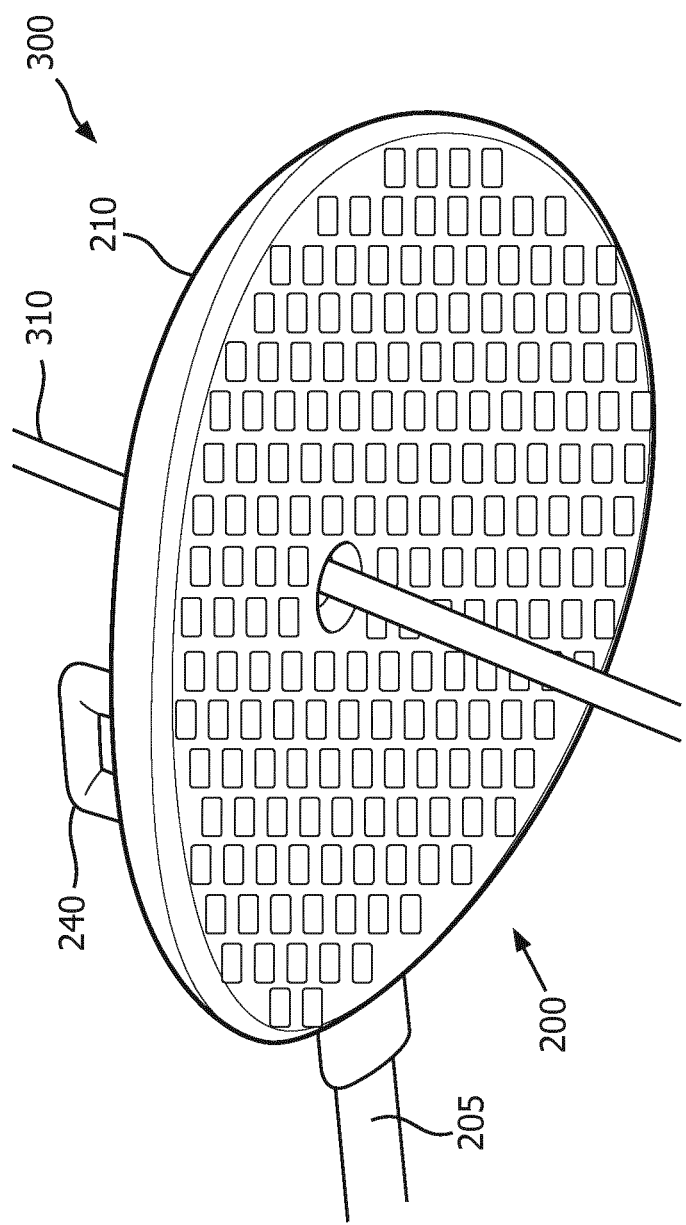
FIG. 3 illustrates example embodiment of an acoustic probe and an interventional device passing through a device insertion port in the acoustic probe.

FIG. 3 illustrates example embodiment of an arrangement 300 of acoustic probe 200 and an interventional device 310 passing through device insertion port 230 of acoustic probe 200. In some embodiments, device insertion port 230 may have a size such that an interventional device 310 having a diameter of 1 cm can pass therethrough. In this embodiment the second diameter of the tapered opening is at least 1 cm, while the second diameter can be above 1 cm or around 2 cm.

Although acoustic probe 200 includes a single device insertion port 230, in other embodiments an acoustic probe may include two or more device insertion port(s) 230. Also, although in acoustic probe 200 device insertion port 230 has a generally circular shape and is disposed at a center of substrate 210, in other embodiments a device insertion port may have a different shape and/or may be located in a different place on the substrate.

Figure 4:
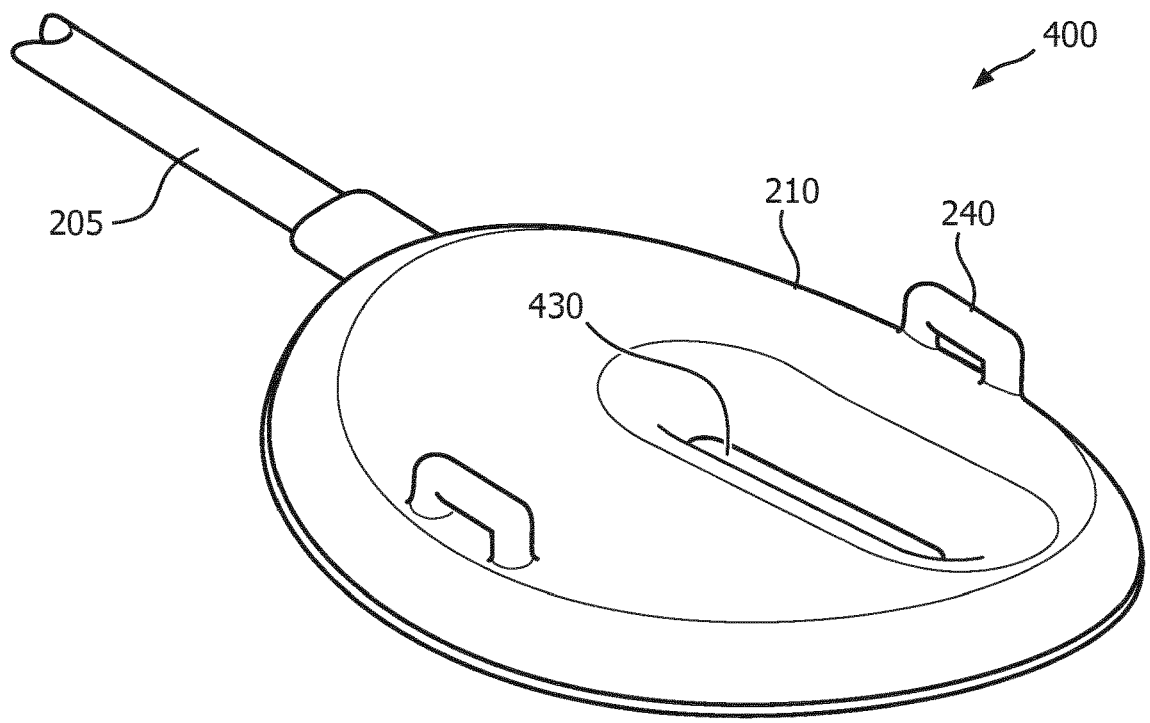
FIG. 4 illustrates another example embodiment of an acoustic probe.

For example, FIG. 4 illustrates another example embodiment of an acoustic probe 400 which includes a device insertion port 430 having the shape of an elongated radial slit or slot, instead of a hole in the center of substrate 210 which only offers a single fixed skin entry point once acoustic probe 200 is fixed to the subject. In this embodiment the device insertion port 430 comprises a tapered opening having the elongated radial shape. The elongated radial shape can be characterized by two radii: maximum radius and minimum radius. The elongated radial shape can be an ellipse. The device insertion port 430 shaped as an elongated radial slot may provide more flexibility for finding a suitable skin insertion point and trajectory for inserting an interventional device into the subject's tissue without having to reposition acoustic probe 400. The tapered opening of the device insertion port 430 has a first surface area (s1) at the first principal surface 212 and a second surface area (s2) at the second principal surface 214, wherein the second area is smaller than the first area. Each surface area of the opening is defined by the corresponding diameters (or radii) of the opening. As in the previous example the surface area of the tapered opening gradually changes from the first surface area (as well as defining said surface radii) to the second surface area while passing through the substrate 210 from the first principal surface 212 to the second principal surface 214. The tapered shape of the device insertion port 430 further allows the user to vary not only the trajectory of insertion of the interventional device but also to have more freedom in selecting the insertion location. The degree of the trajectory variation (or a maximum insertion angle of the interventional device with respect to the subject's surface) would depend on a ratio between the first and the second surface areas (s1/s2) of the tapered opening and/or a thickness of the substrate 210. At a given substrate thickness the maximum insertion angle increases with an increase of said ratio. The tapered interior surface of the device insertion port 430 (as well as 230) allows altering the orientation of the interventional tool and an elongated shape of the opening of the device insertion port 430 provided an additional flexibility in said tool entering point into the subject's tissue. In one of the aspects of the invention the second dimeter is twice as small as the first diameter.

Figure 5:
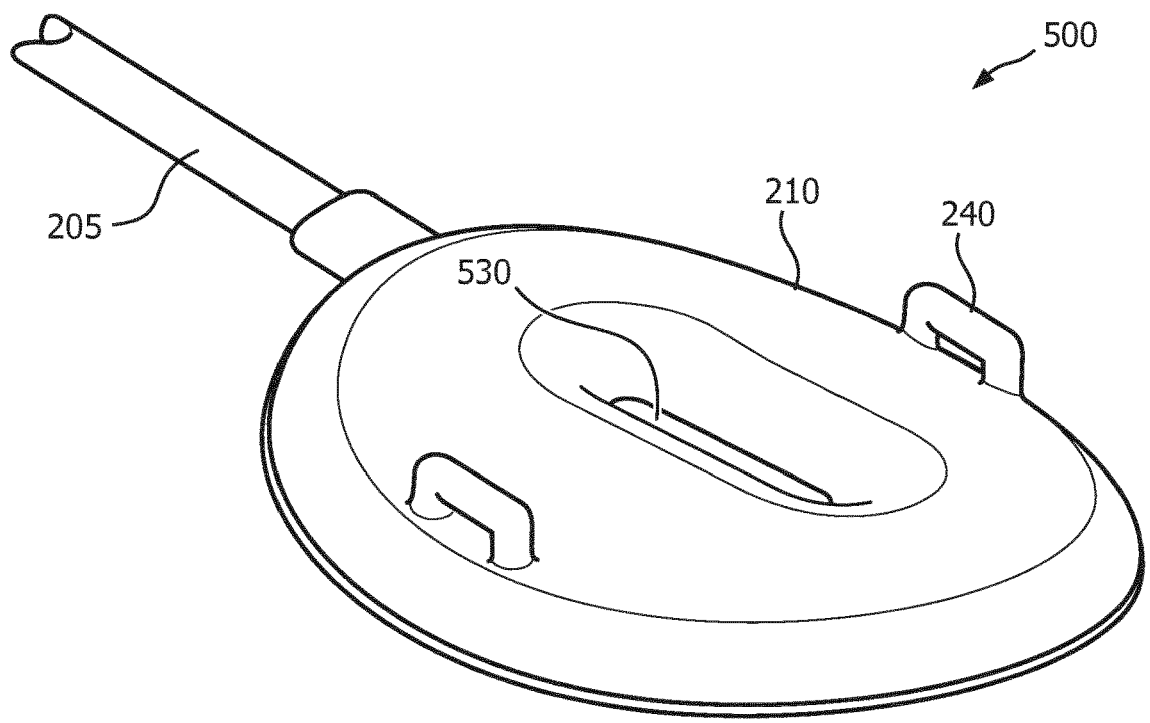
FIG. 5 illustrates yet another example embodiment of an acoustic probe.

FIG. 5 illustrates yet another example embodiment of an acoustic probe 500 with a device insertion port 530 having the shape of a tapered elongated slit or slot. In other embodiments, an acoustic probe may include a plurality of elongated slits or slots extending radially from the center of substrate 210. In other embodiments, an acoustic probe may include one or more device insertion ports having the shape of "x-shaped" tapered slots or slits which may allow an interventional device to be moved in two (e.g., orthogonal) directions within the insertion port to reach a desired insertion location.

Beneficially, acoustic probe 200 (and acoustic probes 400 and 500) may comprise a large transducer array with an imaging aperture which surrounds the insertion location of the interventional device. For example, in some versions, an active area of substrate 210 defined by the array of acoustic transducer elements 222 may have a diameter of at least approximately 12 cm. Beneficially, substrate 210 may have a thickness of approximately 1 cm. Beneficially, substrate 210 may be rigid or semi-rigid.

Some versions of acoustic probe 200 may be employed for abdominal interventions at depths of approximately 8 cm. Interventions that fall in this category may include Chorionic Villus Sampling and fetal interventions such as altering blood flow patterns in twin-to-twin transfusion syndrome (TTTS). Some versions of acoustic probe 200 may be used with an acoustic imaging machine (e.g., acoustic imaging machine 110) to resolve nerve fibers at 8 cm depth.

Operationally, to get sufficient signal at 8 cm depth, the ultrasound center frequency of the acoustic imaging system 100 may be chosen sufficiently low, for example approximately 3.5 MHz or less. Beneficially, in a case where the region of interest is known to be close to 8 cm deep and located relatively close to the central axis of the array of acoustic transducer elements 222, only small steering angles may be required. In this case, the size of acoustic transducer elements 222 may be relatively large and acoustic probe 200 may be operated in a manner similar to a linear array.

Beneficially, acoustic transducer elements 222 have a size of about one wavelength, for example about 0.44 cm when acoustic probe is controlled by an acoustic imaging machine to operate at about 3.5 MHz. In that case, in some versions acoustic probe 200 may have about 60000 acoustic transducer elements populating substrate 210 surrounding device insertion port 230.

If acoustic probe 200 is used with a system (e.g., the acoustic imaging system 100) which allows tracking, then acoustic imaging machine 110 knows the position of the interventional device tip and may only need to image a small area of interest around this tip. In some embodiments, tracking could be done by providing a passive acoustic receiver at or near a distal end of interventional device 310 passing through device insertion port 230 of acoustic probe 200 in the area of interest.

Figure 6:
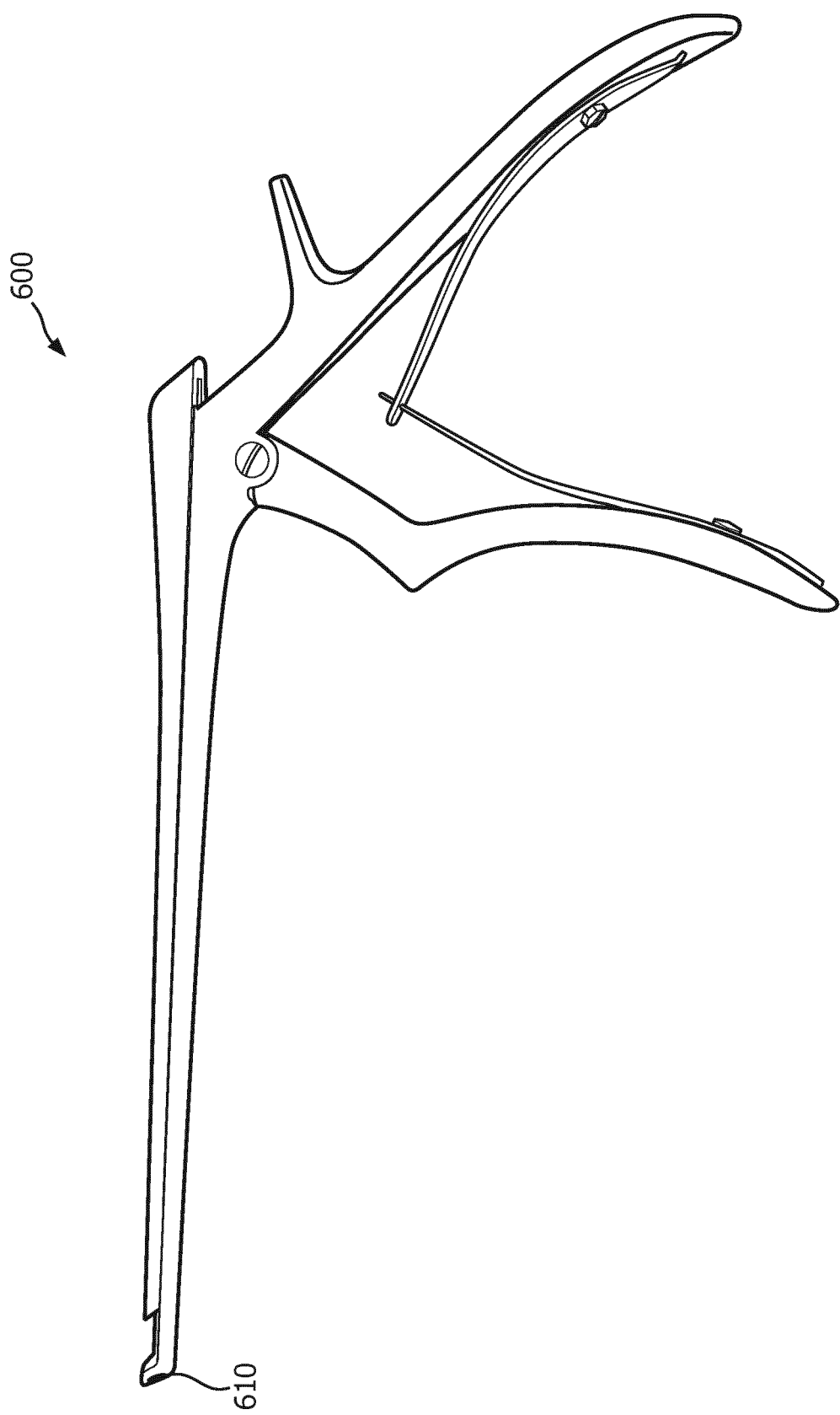
FIG. 6 illustrates one example embodiment of an interventional device having an acoustic receiver disposed at a distal end thereof.

FIG. 6 illustrates one example embodiment of an interventional device 600 having an acoustic receiver (e.g., a passive acoustic receiver) 610 disposed at a distal end thereof. Interventional device 600 may be one embodiment of interventional device 310, and accordingly may be configured to pass through device insertion port 230 of acoustic probe 200. Although only one acoustic receiver 610 is shown for interventional device 600, other embodiments of interventional devices may include two or more acoustic receiver(s) 610.

For real-time guidance of an interventional device employed in an interventional procedure, in some cases it may be sufficient to only image an area of interest comprising a 2×2 cm X-plane at the tip of interventional device 600. This may be achieved by creating an active acoustic aperture of at least approximately 10 cm at any given time, and sliding it over a 2 cm range in lateral and elevational directions over time. The active aperture of the array is defined by the area of the transducers, which are simultaneously activated at the given moment of time for the transmission event.

However, such a large active aperture is, in general, susceptible to aberration artifacts.

Beneficially, in some embodiments such artifacts may be mitigated by processor 112 of acoustic imaging machine 110 using feedback received by receiver interface 118 from one or more passive acoustic receivers 610 on interventional device 600.

With proper aberration correction, this may allow imaging at about twice the depth of a conventional acoustic probe without sacrificing imaging resolution. In general, imaging at twice the depth without losing a significant amount of the available signal requires reducing the central frequency of the acoustic probe signal by a factor of two. Meanwhile, imaging at twice the depth without sacrificing resolution while maintaining the same imaging frequency requires maintaining the same F-number, meaning the active aperture has to span twice as many wavelengths. Combining these two effects, the dimensions of the active aperture should be 2×2=4 times larger to maintain the same imaging resolution at twice the depth. Thus, the resolution of an array of acoustic transducer elements 222 with a 10 cm active aperture at a depth of 8 cm would be comparable to a imaging with a conventional array with a 2.5 cm acoustic aperture at a frequency of 7 MHz at a depth of 4 cm. Furthermore, by coherently summing signals from a larger number of acoustic transducer elements 222, the signal-to-noise ratio (SNR) can be increased.

Figure 7:
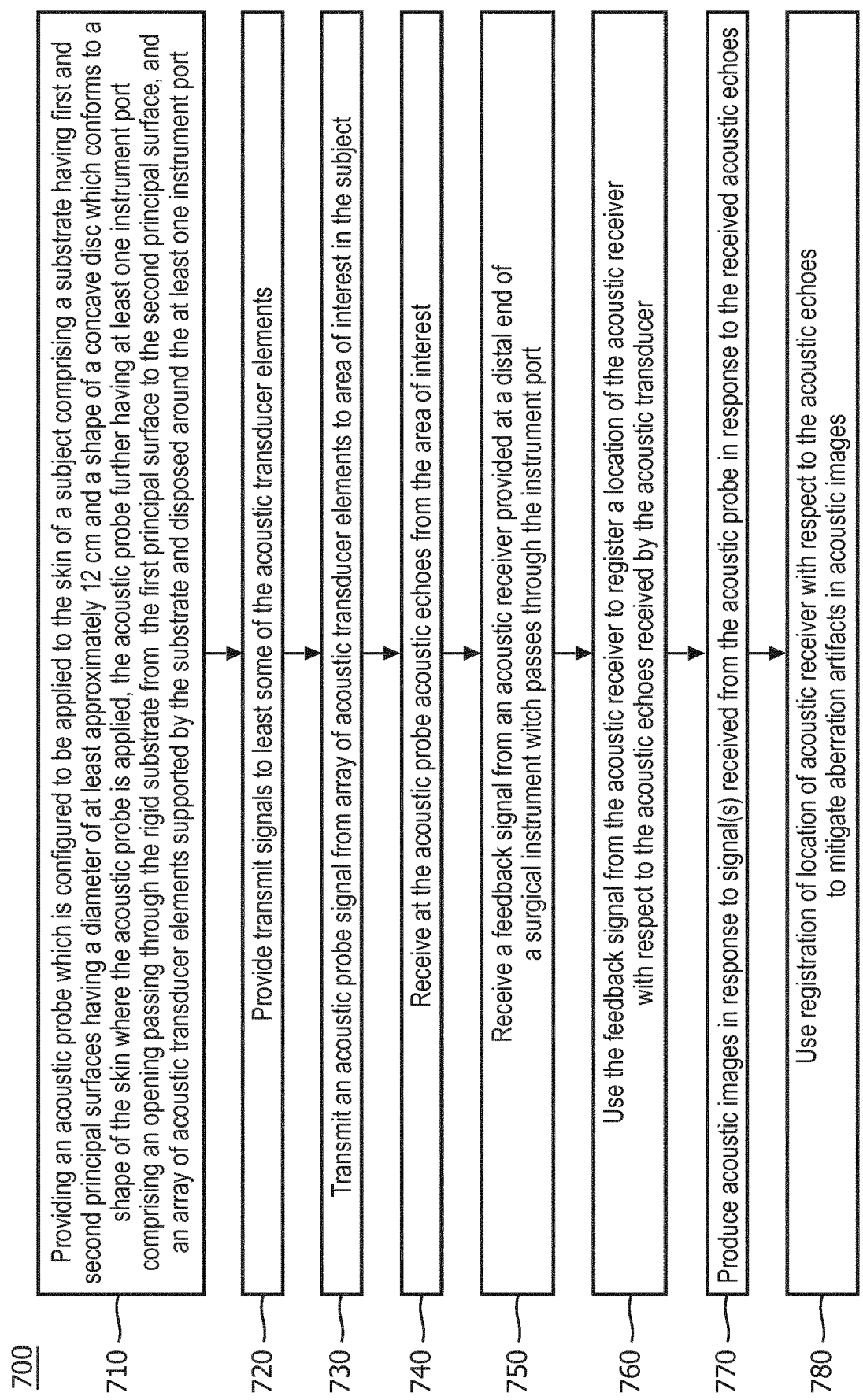
FIG. 7 illustrates a flowchart of one example embodiment of a method of acoustic imaging.

FIG. 7 illustrates a flowchart of one example embodiment of a method 700 of acoustic imaging. To provide a concrete description, reference is made to the acoustic imaging system 100 of FIG. 1 and acoustic probe 200. However, it should be understood that in general the method may be performed by a system having a different configuration than the acoustic imaging system 100, and a different configuration than acoustic probe 200 (e.g., acoustic probes 400 and 500).

An operation 710 may include providing acoustic probe 200 comprising substrate 210 which is configured to be applied to the skin of a subject, where the substrate has first and second principal surfaces 212 and 214 with a diameter of at least approximately 12 cm and a shape of a concave disc which conforms to a shape of the skin where acoustic probe 200 is applied. Here, acoustic probe 200 further has at least one device insertion port 230 comprising an opening passing through substrate 210 from first principal surface 212 to second principal surface 214, and an array of acoustic transducer elements 222 supported by substrate 210 and disposed around the device insertion port(s) 230. Acoustic probe 200 may be applied to the skin of the subject at an area where an interventional procedure is desired to be performed, and fixed in place via a strap or straps passing through attachments 240, for example with Velcro. Also, one or more interventional devices (e.g., interventional device 600) may be inserted and passed through device insertion port(s) 230 and into the tissue of the subject. In some embodiments, processor 112 may determine an orientation or alignment which will enable the interventional device passing through device insertion port 230 to reach a target location in a subject's body for an interventional procedure. In that case, before or while an interventional device is inserted into device insertion port 230, the interventional device may be aligned or oriented with the target location. Embodiments of devices and methods for such orientation or alignment will be described in greater detail below.

In an operation 720, processor 112 of acoustic imaging machine 110 may respond to user instructions received via user interface 114 and/or program instructions stored in memory to transmit signals to least some of the acoustic transducer elements 122 of acoustic probe 200.

In operation 730, in response to signals received from acoustic imaging machine 110, acoustic transducer elements 122 of acoustic probe 200 may form an acoustic probe beam and transmit the acoustic probe beam to an area of interest, for example an area in a human body where an interventional procedure is to be performed.

In an operation 740, some or all of the acoustic transducer elements 122 of acoustic probe 200 may receive acoustic echoes from the area of interest in response to the acoustic probe signal. In response to the acoustic echoes, acoustic probe 200 may transmit one or more signals to processor 112 of acoustic imaging machine 110.

In an operation 750, acoustic imaging machine 110 may receive at receiver interface 118 a feedback signal from an acoustic receiver (e.g., acoustic receiver 610) provided at a distal end of an interventional device (e.g., interventional device 600) which passes through device insertion port 230 of acoustic probe 200.

In an operation 760, acoustic imaging machine 110, and in particular processor 112, may use the feedback signal from acoustic receiver 610 to register a location of the acoustic receiver, and thus the tip of interventional device 600, with respect to the acoustic echoes received by acoustic probe 200 from the region of interest. That is, acoustic imaging machine 110 determines from the feedback signal a position of the tip of interventional device 600 so that it may track this tip and thus it may only image a small region around this tip. In other words, the acoustic imaging machine is arranged to track a relative position of the interventional device with respect to the area of interest. In some embodiments, the tracking protocol may be optimized based on the expected position of the tip of interventional device 600. For example, only a subset of acoustic transducer elements 222 may be chosen to insonify the acoustic receiver(s) 610, to ensure maximum signal on the acoustic receiver(s) 610 based on a directivity profile of acoustic receiver(s) 610. This may help increase the tracking sensitivity and SNR.

In an operation 770, acoustic imaging machine 110, and in particular processor 112, may produce acoustic images of the area of interest in response to the one or more signals received from acoustic probe 200 in response to the received acoustic echoes from the area of interest. These acoustic images including the interventional device's location may be displayed to a physician on display 116 for guiding an interventional procedure being performed by the physician in the area of interest which is being imaged.

In an operation 780, acoustic imaging machine 110, and in particular processor 112, may use the registration of the location of acoustic receiver(s) 610 with respect to the acoustic echoes to mitigate aberration artifacts in the acoustic images.

As noted above, one desirable attribute for an acoustic imaging system and method is hands free operation of the acoustic probe.

In particular, when using ultrasound imaging to guide one or more interventional devices (e.g., surgical tools) in a minimally invasive surgical procedure, hands free operation of the acoustic probe is desired so that a sonographer is not needed in addition to the physician/surgeon. However, during a procedure there may however be a moment where the surgeon that is holding the interventional device at the desired location wants or needs to use her/his hands for a different task without disturbing the position of the interventional device. This could for example involve manipulating the position of a second interventional device, manipulating settings on the imaging machine, or inserting a guidewire.

Figure 8:
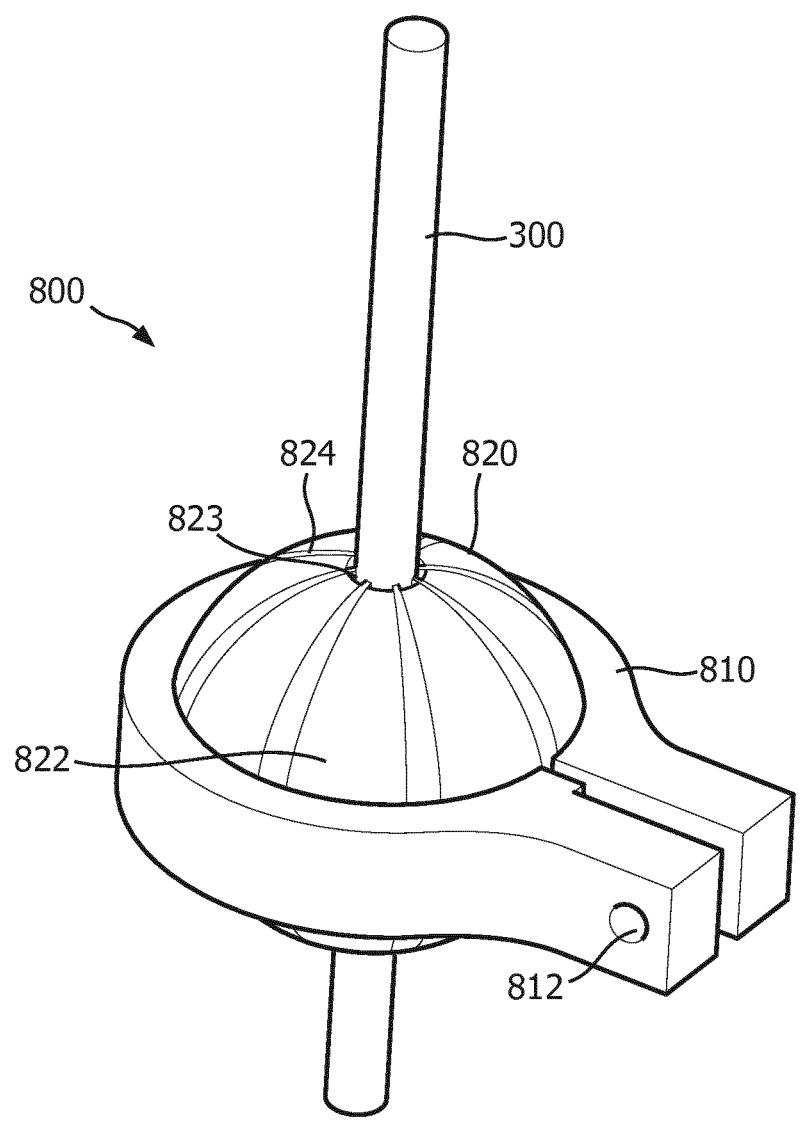
FIG. 8 illustrates an example embodiment of an instrument guide for a device insertion port of an acoustic probe.

To this end, FIG. 8 illustrates an example embodiment of an instrument guide 800 for a device insertion port (e.g., device insertion port 230) of an acoustic probe (e.g., acoustic probe 200).

Figure 9:
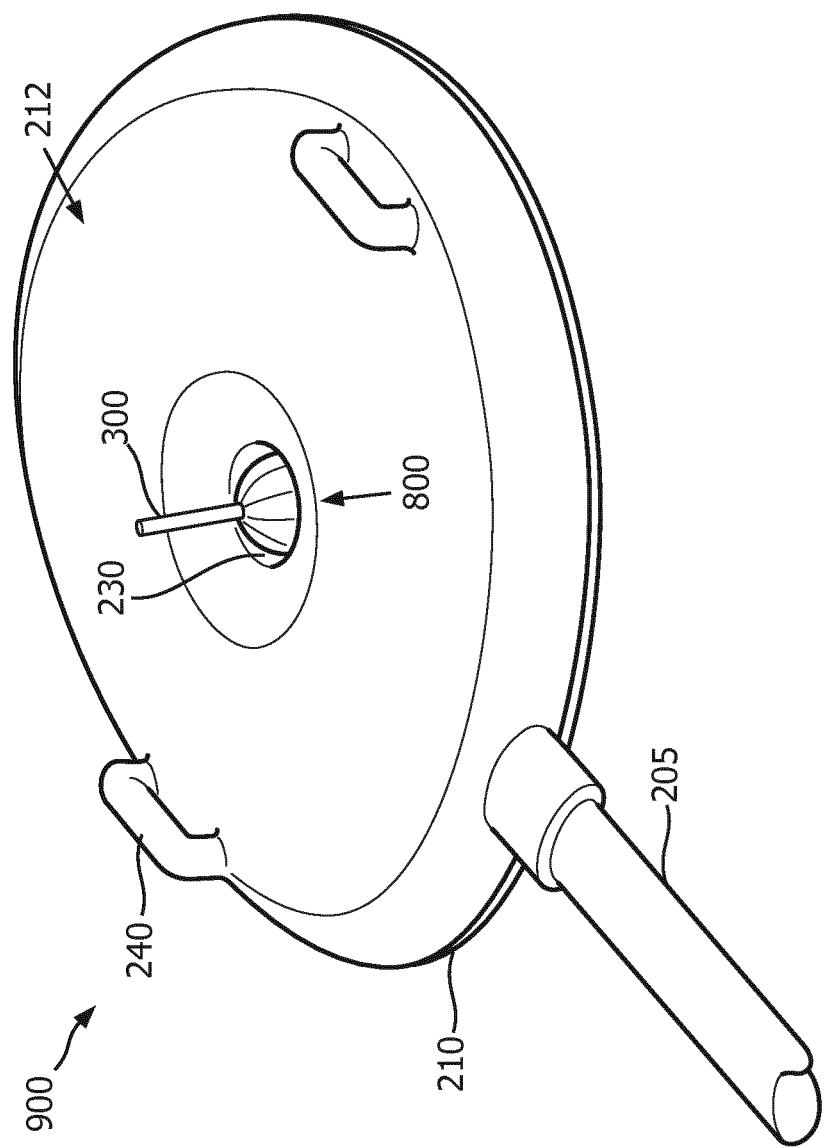
FIG. 9 illustrates an example arrangement of an acoustic probe with a device insertion port and an instrument guide disposed in the device insertion port.

FIG. 9 illustrates an example embodiment of an arrangement 900 of acoustic probe 200, instrument guide 800 disposed in device insertion port 230, and interventional device 310 disposed to pass through instrument guide 800. It should be understood that similar arrangements can be provided for acoustic probes 400 and 500, and for other acoustic probes with different configurations of one or more device insertion ports. It should also be understood, that instrument guide 800 may be integrated with acoustic probe 200 and therefore considered to be part of the acoustic probe, or may be a separate element which is removably inserted in device insertion port 230.

Instrument guide 800 comprises:

an insertion port structure 820 (also referred to as ball structure 820 below) having a cylindrical (or another shape) hole 823 for interventional device 310 to pass therethrough; and an adjustable clamp 810 having a function of a locking unit which at least partially surrounds ball structure 820. The adjustable clamp 810 has a spherical interior surface and is mounted to the interior surface of device insertion port 230. The insertion port structure of 820 can be ball shaped or have a conical shape in order to be more structurally compatible with the shape of the tapered opening of the insertion port. The adjustable clamp 810 may also have an elliptical shape. In some versions, cylindrical hole 823 has a diameter which allows an interventional device 310 having a diameter of at least about 1.5 mm to pass therethrough. Ball structure 820 may include a plurality of larger semi-soft deformable segments 822, and smaller rigid segments 824. In some versions, plurality of larger semi-soft deformable segments 822 may be made out of porous Teflon, and smaller rigid segments 824 be made out of stainless steel. Beneficially, adjustable clamp 810 has a spherical inside surface, with a loose enough fit such that ball structure 820 may rotate freely and interventional device 310 may freely slide in and out of instrument guide 800.

In operation, instrument guide 800 allows free movement of interventional device 310 which is inserted therein until it is put in locking mode by the locking unit and when locked then interventional device 310 is securely held in place (at a fixed position). More specifically, when adjustable clamp 810 is loosened then ball structure 820 can rotate freely within adjustable clamp 810 and an insertion depth of interventional device 310 within instrument guide 800 may be adjusted. However, when adjustable clamp 810 is tightened then ball structure 820 is immobilized within adjustable clamp 810 and an insertion depth of interventional device 310 within instrument guide 800 is locked.

To lock interventional device 310 in instrument guide 800, adjustable clamp 810 may be squeezed together from the protruding ends where thru holes 812 are located. In various embodiments, this could for example be achieved with a nut/bolt structure, a mechanism similar to that employed with a bicycle cable, an electromagnetic actuator, etc. When adjustable clamp 810 is squeezed, it locks ball structure 820 in place, and also pushes smaller rigid segments 824 against interventional device 310 to lock the insertion depth.

In some embodiments, a foot pedal may be employed by a user (e.g., physician/surgeon) to selectively tighten and loosen adjustable clamp 810 to lock and unlock instrument guide 800. In other embodiments, acoustic imaging machine 110 may respond to a voice command from the user to selectively tighten and loosen adjustable clamp 810 to lock and unlock instrument guide 800. In still other embodiments, locking of adjustable clamp 810 may be initiated by an acoustic (ultrasound) scanner, to avoid locking the interventional device in certain critical areas.

Many variations and different embodiments of an instrument guide and an acoustic probe including an instrument guide are possible.

In some embodiments the shape and/or dimensions of the hole in the instrument guide may be adapted to the shape and/or if a particular interventional device to be inserted.

In some embodiments, an instrument guide may be fixed in place by magnetizing it with an electromagnet.

In some embodiments, an acoustic probe may have multiple instrument ports and some or all of the instrument ports may be equipped with an instrument guide.

In some embodiments, an instrument guide may include a disposable ball structure, to aid in maintaining sterility in a surgical environment.

In some embodiments, an instrument guide may be configured to provide separate, independent, locking of the orientation or direction of the hole in the instrument guide in which the interventional device is inserted, and locking of the interventional device inserted within the hole.

When inserting an interventional device inserted within an instrument guide in device insertion port of an acoustic probe, it may be challenging to determine the correct orientation or angulation needed for an interventional device to reach a certain anatomical target location in the acoustic image.

Accordingly, described below is a system and acoustic probe which includes a device insertion port and an encoded and adjustable instrument guide which can communicate with an acoustic imaging machine to automatically determine the optimal insertion orientation for the interventional device, and a method to automatically or manually optimize the orientation of the instrument guide so that an interventional device inserted through the instrument guide in that orientation will intersect with a user-defined target anatomical location in the acoustic image. This can reduce the incidence of repeated device insertions, thus reducing trauma to the subject, improving the clinical workflow, and enabling more accurate interventions.

Figure 10:
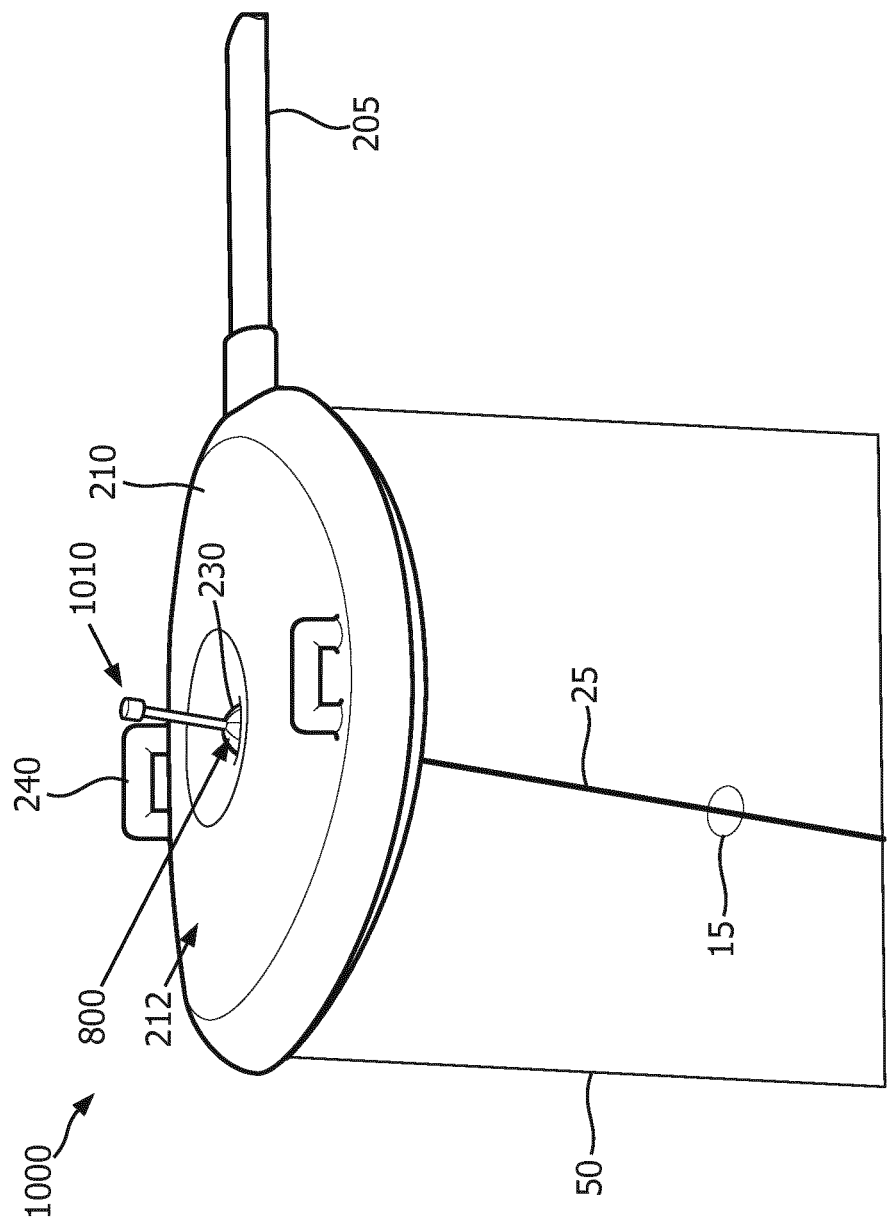
FIG. 10 illustrates an example operation of orienting an instrument guide disposed in a device insertion port of an acoustic probe to position an interventional device tip at a desired location.

FIG. 10 illustrates an example operation of orienting an instrument guide disposed in a device insertion port of an acoustic probe to position an interventional device tip at a desired target location within an area of interest which is being acoustically imaged in a subject. To provide a concrete description, reference is made to the acoustic imaging system 100 of FIG. 1 and arrangement 1000, which is a combination of acoustic probe 200, instrument guide 800 and a joystick 1010. However, it should be understood that in general the operation may be performed by an arrangement having a different configuration than arrangement 1000, and a different configuration than acoustic probe 200 (e.g., acoustic probes 400 and 500).

FIG. 10 shows an acoustic imaging plane 50 and a joystick 1010 which may be used for maneuvering instrument guide 800 to a desired orientation which may have been computed by processor 112 of acoustic imaging machine 110 to place the tip of an interventional device at a target location 15.

In operation, once acoustic probe 1100 has been satisfactorily positioned on the subject of an interventional procedure, then a clinician/surgeon may define target location 15 within the area of interest of acoustic imaging plane 50, for example, by clicking a point or drawing a target location or region on an ultrasound image via user interface 114 and display 115. Processor 112 may then retrieve target location 15 from the acoustic scanner. Since instrument guide 800 is attached to, and hence, registered to, the array of acoustic transducer elements 222 of acoustic probe 200, processor 112 may automatically compute the orientation of instrument guide 800 which is needed to enable the interventional device 310 to reach target location 15.

In some embodiments, the orientation of instrument guide 800 may be defined by an encoder provided with instrument guide 800.

In one embodiment of an encoder, ball structure 820 may have a unique spatially varying optical pattern provided (e.g., painted) on it which may be read out using a high resolution miniature camera embedded in adjustable clamp 810. Such pattern may, for example, be a grid of latitude and longitude lines with line thicknesses depending on longitude and latitude coordinates. For further differentiation the longitude lines may also have a different color then the latitude lines. Such an arrangement may provide three degrees of freedom (i.e., tip/tilt/rotation) for moving ball structure 820. In that case, processor 112 may calculate the desired orientation of instrument guide 800 and associated encoder value(s), and may automatically maneuver instrument guide 800 to have the calculated orientation via feedback by comparing the actual encoder value(s) to the calculated encoder value(s). In some embodiments, this may be done before the interventional device is introduced through instrument guide 800. Electronic communication between processor 112 and instrument guide 800 may be enabled using wired connections that can be included in the side-mounted flat probe cable 205. Once instrument guide 800 has been adjusted to the desired orientation, the interventional device may be inserted as needed.

Some embodiments may utilize additional encoding for the process of inserting interventional device at target location 15 in the subject. For example, in some embodiments the interventional device may have one or more length markers as well as small grooves for length approximation and locking the interventional device. Length and angle measurements based on these length marker(s) and/or small grooves may be used for approximating the orientation and position of the interventional device.

In another embodiment, processor 112 may calculate the desired orientation of instrument guide 800 and associated encoder value(s), and the user may manually maneuver instrument guide 800 (e.g., via joystick 1010) to match the calculated encoder value(s).

To aid in manual adjustment of instrument guide 800, joystick 1010 may be temporarily attached to instrument guide 800. Once the orientation/adjustment process is complete, joystick 1010 can be removed and replaced by the interventional device. In another embodiment, joystick 1010 may have a hollow channel through which the interventional device may be inserted, which may allow the interventional procedure to be performed without having to remove joystick 1010. Alternatively, joystick 1010 may be permanently attached to instrument guide 800 in an aligned orientation, but translated slightly relative to the insertion point of the interventional device to allow insertion of the interventional device.

During manual adjustment of instrument guide 800, a projected tool path 25 may be displayed on display 116 and may be continuously updated so that the user can also use this as feedback to correctly align instrument guide 800. In some cases, if the required adjustments are out of acoustic imaging plane 50, it may not be possible to use only image-based feedback to align instrument guide 800.

Figure 11:
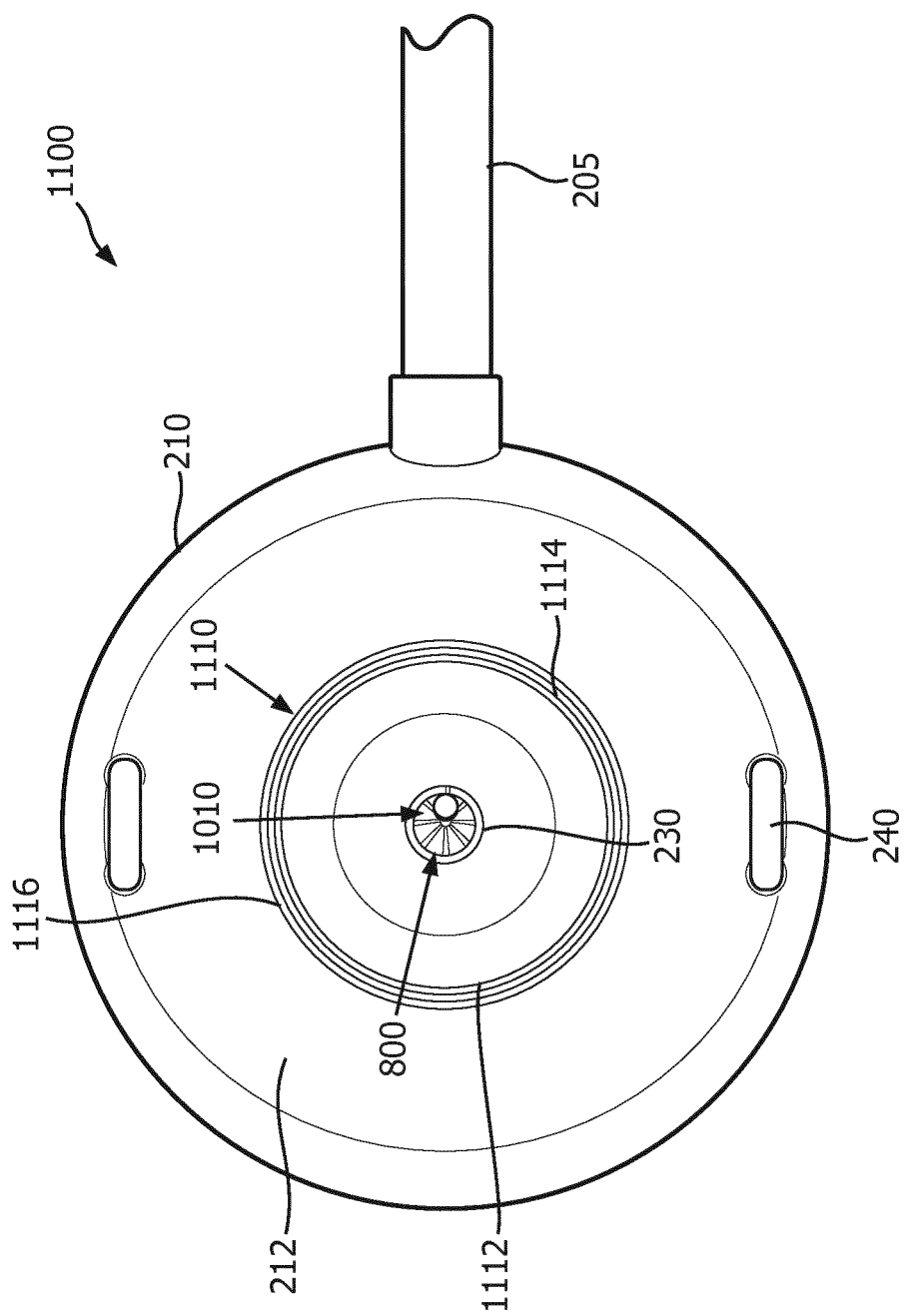
FIG. 11 illustrates yet another example embodiment of an acoustic probe with a device insertion port and an instrument guide disposed in the device insertion port.

To aid in out-of-plane adjustments, FIG. 11 illustrates yet another example embodiment of an acoustic probe 1100 with device insertion port 230 and instrument guide 800 disposed in device insertion port 230. The probe of this embodiment further comprises user feedback arrangement enabling the user to orient the interventional device within the instrument guide towards the target location. The upper surface of substrate 210 of acoustic probe 1100, surrounding device insertion port 230, is fitted with three circular concentric rings of light elements (e.g., light emitting diodes (LEDs), which provide a visual feedback to the user) 1100 of different colors. For example, in some embodiments an innermost ring 1112 of LEDs may be yellow, a middle ring 1114 may be green, and an outermost ring 1116 may be red. These LED lights may serve as guidance while the user is maneuvering instrument guide 800 to a desired orientation in device insertion port 230. In some embodiments, at any given time only one LED may be illuminated to indicate a direction in which the user should maneuver instrument guide 800.

Figure 12:
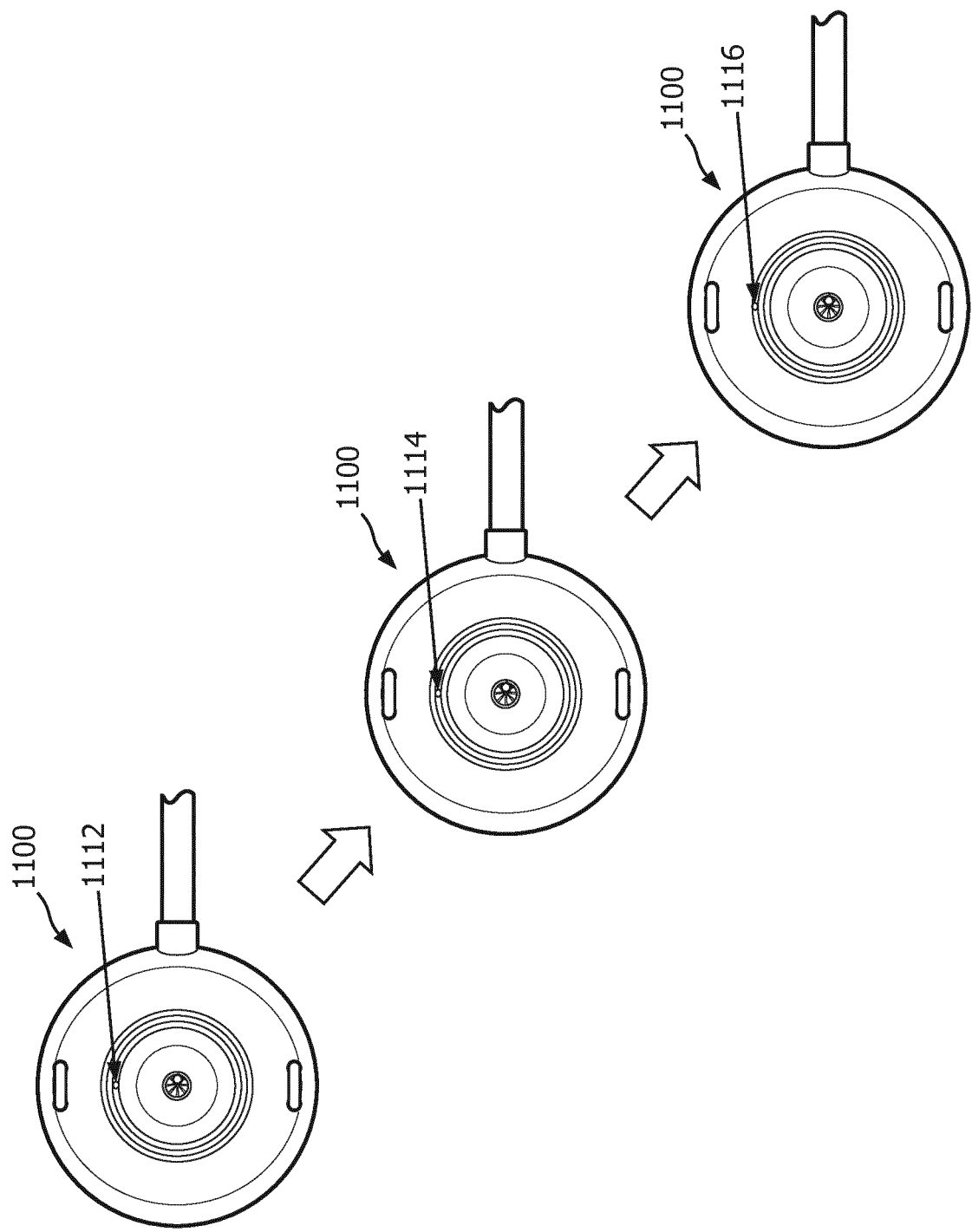
FIG. 12 illustrates a process of providing user feedback while orienting an instrument guide disposed in a device insertion port of an acoustic probe to position an interventional device tip at a desired location.

FIG. 12 illustrates a process of providing user feedback while orienting instrument guide 800 disposed in device insertion port 230 of acoustic probe 1100 to position an interventional device tip at target location 15.

Once processor 112 calculates the encoder value(s) for instrument guide 800, an LED for indicating the appropriate orientation may be activated as follows. First, a yellow LED of innermost ring 1112 in the determined direction may be activated, indicating to the user that the instrument guide 800 needs to be pivoted in that direction. Once the user has pivoted instrument guide 800 by the correct amount as determined by processor 112, the yellow LED of innermost ring 1112 may be deactivated and a green LED of middle ring 1114 may be activated, indicating that instrument guide 800 is in the optimal orientation as determined by processor 112. If the user overshoots the target and pivots instrument guide 800 too much, then the green LED of middle ring 1114 may be deactivated and a red LED of outermost ring 1116 may be activated, indicating that the user has pivoted instrument guide 800 too much. Optionally, at this stage, a yellow LED in the diametrically opposite location may also be activated, indicating that the user has to now pivot instrument guide 800 back in the opposite direction to reach the optimal orientation.

As in the case of automatic orientation of instrument guide 800 by processor 112, once instrument guide 800 has been adjusted to the desired orientation, instrument guide 800 may be held steady in the desired orientation as described above, and the interventional device may be inserted as needed.

In some embodiments, the LED-based workflow described above with respect to FIG. 12 may be used for coarse adjustment of the orientation of instrument guide 800, and the current encoder values (and the desired optimal encoder values) may also be displayed on display 115 to allow the user to further fine-tune the orientation of instrument guide 800, if needed. In some embodiments, acoustic imaging machine 110 may provide audio feedback (for example, a beep) to a user to indicate that the optimal orientation of instrument guide 800 has been reached.

Depending on the shape of the device insertion port containing instrument guide 800, instrument guide 800 may be adjusted in multiple ways with different available degrees of freedom (DOF) for maneuvering an interventional device inserted through it.

For example, in embodiments where instrument guide 800 only can be tipped and tilted (pitch and yaw), but is not translatable, within the device insertion port (e.g., device insertion port 230), then there will be 4 DOF for maneuvering the interventional device.

In other embodiments where instrument guide 800 can be translated along one axis (e.g., device insertion port 430 or 539), then there will be 5 DOF for maneuvering the interventional device.

In yet other embodiments where instrument guide 800 can be translated along two perpendicular axis (e.g., the device insertion port is an X-shaped slit or slot), then there will be 6 DOF for maneuvering the interventional device.

In some embodiments, tracking of the interventional device along the projected tool path 25 can be accomplished using acoustic (e.g., ultrasound) tracking (InSitu), in which one or more acoustic sensors on the shaft of the interventional device are tracked within the acoustic images. The extent of insertion of the interventional device within the instrument guide can also be quantified using an encoder on the instrument guide, for example using length markers described above. While this method will not account for any bending of the interventional device, it can serve as a good initial approximation for the position of the tip of the interventional device, which then may be utilized by other tracking methods such as InSitu.

While preferred embodiments are disclosed in detail herein, many variations are possible which remain within the concept and scope of the invention. Such variations would become clear to one of ordinary skill in the art after inspection of the specification, drawings and claims herein. The invention therefore is not to be restricted except within the scope of the appended claims.

The invention claimed is:

1. An acoustic probe for application with an interventional device, comprising:
   a substrate having a first principal surface and a second principal surface, and further having at least one device insertion port comprising a tapered opening passing through the substrate from the first principal surface to the second principal surface;
   an instrument guide comprising an encoder, which comprises a spatially varying optical pattern comprising a grid of latitude and longitude lines with line thicknesses depending on longitude and latitude coordinates, and arranged to indicate an orientation of the instrument guide within the at least one device insertion port, wherein the instrument guide is disposed within the device insertion port, the instrument guide being configured to selectively allow the interventional device to move freely within the device insertion port to achieve a desired angular orientation; and
   an array of acoustic transducer elements supported by the substrate and defining an area of the substrate, said array of acoustic transducer elements disposed around the at least one device insertion port.

2. The acoustic probe of claim 1, wherein the device insertion port is located in a center of the substrate.

3. The acoustic probe of claim 1, wherein the substrate has a shape of a concave disc.

4. The acoustic probe of claim 1, wherein an active area of the substrate defined by the array of acoustic transducer elements has a diameter of at least approximately 12 cm.

5. The acoustic probe of claim 1, wherein the tapered opening comprises a first diameter at the first principal surface and a second diameter at the second principal surface, wherein the second diameter is smaller than the first diameter.

6. The acoustic probe of claim 5, wherein a diameter of the tapered opening gradually changes from the first diameter to the second diameter while passing through the substrate from the first principal surface to the second principal surface.

7. The acoustic probe of claim 1, wherein the instrument guide comprises a locking unit configured to selectively lock the interventional device within the device insertion port in response to a user input via a user interface connected to the acoustic probe.

8. The acoustic probe of claim 1, wherein the instrument guide comprises:
   an insertion port structure having a hole for the interventional device to pass therethrough; and
   an adjustable clamp at least partially surrounding the insertion port structure, the adjustable clamp being mounted to an interior surface of the device insertion port,
   wherein when the adjustable clamp is loosened the insertion port structure is adapted to move freely within the adjustable clamp and an insertion depth of the interventional device within the instrument guide may be adjusted, and
   wherein when the adjustable clamp is tightened the insertion port structure is immobilized within the adjustable clamp and an insertion depth of the interventional device within the instrument guide is locked.

9. The acoustic probe of claim 8, wherein the insertion port structure includes a first plurality of relatively rigid segments and a second plurality of relatively soft segments.

10. The acoustic probe of claim 8, wherein the insertion port structure has disposed thereon an optical pattern, and wherein the adjustable clamp has an optical detector provided therein for reading the optical pattern and providing an output signal indicating an orientation of the insertion port structure within the adjustable clamp.

11. The acoustic probe of claim 8, further comprising a user feedback arrangement coupleable to an imaging system and adapted to enable a user to orient the interventional device within the instrument guide towards a target location.

12. The acoustic probe of claim 11, wherein the user feedback arrangement comprises circular concentric rings of light elements disposed around the device insertion port on at least one of the first and second principal surfaces of the substrate.

13. The acoustic probe of claim 1, further comprising at least a second device insertion port comprising at least a second opening passing through the substrate from the first principal surface to the second principal surface.

14. The acoustic probe of claim 1, wherein the device insertion port comprises an elongated tapered slot.

15. The acoustic probe of claim 8, wherein the adjustable clamp comprises a spherical interior surface.

16. An acoustic probe for application with an interventional device, comprising:
   a substrate having a first principal surface and second principal surface, and further having at least one device insertion port comprising a tapered opening passing through the substrate from the first principal surface to the second principal surface;

an instrument guide comprising an encoder, which comprises a spatially varying optical pattern comprising a grid of latitude and longitude lines with line thicknesses depending on longitude and latitude coordinates and arranged to indicate an orientation of the instrument guide within the at least one device insertion port, wherein the instrument guide is disposed within the device insertion port, the instrument guide being configured to selectively allow the interventional device to move freely within the device insertion port to achieve a desired angular orientation;

a processor;

a tangible non-transitory computer-readable medium that stores instructions, which when executed by the processor, cause the processor to determine a desired orientation of instrument guide within the device insertion port; and an array of acoustic transducer elements supported by the substrate and defining an area of the substrate, said array of acoustic transducer elements disposed around the at least one device insertion port.

17. The acoustic probe of claim 16, wherein the instructions, when executed by the processor, further cause the processor to determine an encoder value associated with a desired position.

18. The acoustic probe of claim 17, wherein the instructions, when executed by the processor, further cause the processor to cause a controller to maneuver the instrument guide to have the determined orientation of the instrument guide by comparing an actual encoder value to the determined encoder value associated with a desired position.

19. The acoustic probe of claim 16, wherein the instrument guide comprises:

an insertion port structure having a hole for the interventional device to pass therethrough; and an adjustable clamp at least partially surrounding the insertion port structure, the adjustable clamp being mounted to an interior surface of the device insertion port, wherein when the adjustable clamp is loosened the insertion port structure is adapted to move freely within the adjustable clamp and an insertion depth of the interventional device within the instrument guide may be adjusted, and wherein when the adjustable clamp is tightened the insertion port structure is immobilized within the adjustable clamp and an insertion depth of the interventional device within the instrument guide is locked.

20. The acoustic probe of claim 19, wherein the insertion port structure includes a first plurality of relatively rigid segments and a second plurality of relatively soft segments.

21. The acoustic probe of claim 19, wherein the insertion port structure has disposed thereon an optical pattern, and wherein the adjustable clamp has an optical detector provided therein for reading the optical pattern and providing an output signal indicating an orientation of the insertion port structure within the adjustable clamp.

22. The acoustic probe of claim 16, further comprising a user feedback arrangement coupleable to an imaging system and adapted to enable a user to orient the interventional device within the instrument guide towards a target location.

23. The acoustic probe of claim 22, wherein the user feedback arrangement comprises circular concentric rings of light elements disposed around the device insertion port on at least one of the first and second principal surfaces of the substrate.

24. The acoustic probe of claim 16, further comprising at least a second device insertion port comprising at least a second opening passing through the substrate from the first principal surface to the second principal surface.

25. The acoustic probe of claim 16, wherein the instrument guide further configured to selectively allow the interventional device to rotate freely within the device insertion port to achieve a desired angular orientation.

26. The acoustic probe of claim 1, wherein the instrument guide further configured to selectively allow the interventional device to rotate freely within the device insertion port to achieve a desired angular orientation.

* * * * *